United States Patent
Fu

(10) Patent No.: US 6,887,868 B2
(45) Date of Patent: May 3, 2005

(54) THERAPEUTIC 5-HT LIGAND COMPOUNDS

(75) Inventor: Jian-Min Fu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 51 days.

(21) Appl. No.: 10/247,756

(22) Filed: Sep. 19, 2002

(65) Prior Publication Data

US 2003/0087883 A1 May 8, 2003

Related U.S. Application Data

(60) Provisional application No. 60/323,666, filed on Sep. 21, 2001.

(51) Int. Cl.[7] ............. C07D 491/06; C07D 487/06; A61K 31/5383; A61K 31/542; A61P 25/24
(52) U.S. Cl. .............. 514/230.2; 544/101; 544/32; 540/468; 540/472; 540/477; 540/547; 540/556; 540/581; 546/94; 548/150; 548/217; 548/302.4; 548/428
(58) Field of Search .................... 544/101; 514/230.2

(56) References Cited

U.S. PATENT DOCUMENTS

| | | | |
|---|---|---|---|
| 4,219,550 A | 8/1980 | Rajagopalan | 424/246 |
| 4,938,949 A | 7/1990 | Borch et al. | 424/10 |

FOREIGN PATENT DOCUMENTS

| | | |
|---|---|---|
| DE | 2 330 719 | 1/1974 |
| EP | 0 322 016 | 6/1989 |
| EP | 0 393 766 | 10/1990 |
| EP | 0 403 261 | 12/1990 |
| EP | 0 473 550 A1 | 3/1992 |
| WO | WO 00/06564 | 2/2000 |
| WO | WO 00/64899 | 11/2000 |
| WO | WO 00/77010 A2 | 12/2000 |

OTHER PUBLICATIONS

Total Synthesis of Heptacyclic Aspidosperma Alkaloids, Part 1, Preliminary Experiments, John W. Blowers, et al., J. Chem. Soc. Perkins Trans. 1 1987, pp. 2079–2090 (12 sheets).

(+)-cis–4, 5, 7a, 8, 9, 10, 11, 11a–Octahydro–7H– 10–methylindolo [1, 7–bc] [2,6]–napthyridine: A 5–$HT_{2C/2B}$ Receptor Antagonist with Low 5–$HT_{2A}$ Receptor Affinity, J. Med. Chem., vol. 38, No. 1, 1995, pp. 28–33 (6 sheets).

5–$HT_6$ Serotonin Receptor Binding of Indolealkyamines: A Preliminary Structure–Affinity Investigation, Med. Chem. Res., vol. 9, No. 2, 1999, pp. 108–117 (10 sheets).

*Primary Examiner*—Mark L. Berch
*Assistant Examiner*—Kahsay Habte
(74) *Attorney, Agent, or Firm*—Flynn, Thiel, Boutell & Tanis, P.C.

(57) ABSTRACT

The present invention provides compounds of Formula (I):

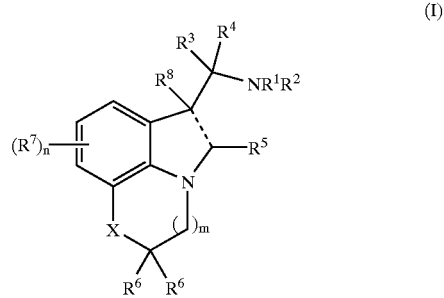

(I)

wherein: $R^1, R^2, R^3, R^4, R^5, R^6, R^7, R^8$, n, m, and X have any of the values defined in the specification, as well as pharmaceutical compositions comprising the compounds. The invention also provides therapeutic methods as well as processes and intermediates useful for preparing compounds of Formula (I). The compounds are 5-HT ligands and are useful for treating diseases wherein modulation of 5-HT activity is desired.

34 Claims, No Drawings

THERAPEUTIC 5-HT LIGAND COMPOUNDS

CROSS-REFERENCE TO RELATED APPLICATIONS

This application claims the benefit of U.S. provisional application Ser. No. 60/323,666 filed on 21 Sep. 2001, under 35 USC 119(e)(i), which is incorporated herein by reference in its entirety.

FIELD OF THE INVENTION

The present invention provides tricyclic indole and indoline derivatives, and more specifically, provides compounds of Formula (I) described herein below. These compounds are 5-HT ligands, and are useful for treating diseases wherein modulation of 5-HT activity is desired.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. See R. W. Fuller, Biology of Serotonergic Transmission, ed. Neville V. Osborne, John Wiley and Sons (1982), p 221; D. J. Boullin, Serotonin in Mental Abnormalities 1, John Wiley and Sons (1978), p. 316; J. Barchas, et al., Serotonin and Behavior, Accademic Press, New York, N.Y. (1973). N. M. Barnes; T. Sharp, A review of central 5-HT receptors and their function, Neuropharmacology, 1999, 38, 1083–1152. Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting. See M. D. Gershon, et al., The Peripheral Actions of 5-Hydroxytryptamine, 246 (1989); P. R. Saxena, et al., Journal of Cardiovascular Pharmacology, 15: Supplement 7 (1990).

The major classes of serotonin receptors (5-HT1–7) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203. Recently discovered information regarding subtype identity, distribution, structure, and function suggests that it is possible to identify novel, subtype specific agents, having improved therapeutic profiles (e.g. fewer side effects).

For example, the 5-HT$_2$ family of receptors is comprised of 5-HT$_{2A}$, 5-HT$_{2B}$, and 5-HT$_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three 5-HT$_2$ subtypes. The 5-HT$_{2B}$ and 5-HT$_{2A}$ receptors are widely distributed in the periphery, while the 5-HT$_{2C}$ receptor has been found only in the central nervous system, being highly expressed in many regions of the human brain. See G. Baxter, et al. Trends in Pharmacol. Sci. 1995, 16, 105–110.

Subtype 5-HT$_{2A}$ has been associated with effects including vasoconstriction, platelet aggregation, and bronchoconstriction, while subtype 5-HT$_{2C}$ has been associated with diseases that include depression, anxiety, obsessive compulsive disorder, panic disorders, phobias, psychiatric syndromes, and obesity. Very little is known about the pharmacological role of the 5-HT$_{2B}$ receptor. See F. Jenck, et al., Exp. Opin. Invest. Drugs, 1998, 7, 1587–1599; F. Jenck, et al., J. Med. Chem., 1997, 40, 2762–2769; J. R. Martin, et al., The Journal of Pharmacology and Experimental Therapeutics, 1998, 286, 913–924; S. M. Bromidge, et al., J. Med. Chem., 1998, 41, 1598–1612; G. A. Kennett, IDrugs, 1998, 1, 4, 456–470; and A. Dekeyne, et al., Neuropharmacology, 1999, 38, 415–423; M. Isaac, Drugs of the Future, 2001, 26, 383–393.

There is currently a need for pharmaceutical agents that are useful to treat diseases and conditions that are associated with 5-HT receptors.

SUMMARY OF INVENTION

A compound of Formula I:

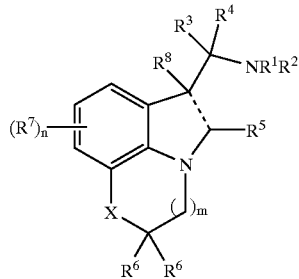

wherein:

$R^1$ and $R^2$ are independently hydrogen, $C_{1-8}$alkyl, substituted $C_{1-8}$alkyl, aryl($C_{1-8}$)alkylene, cycloalkyl, substituted cycloalkyl or heteroaryl($C_{1-8}$)alkylene;

$R^3$ and $R^4$ are independently hydrogen, $C_{1-8}$alkyl, aryl ($C_{1-8}$)alkylene, or heteroaryl($C_{1-8}$)alkylene;

$R^5$ and each $R^6$ are independently hydrogen, $C_{1-8}$alkyl, aryl, heteroaryl, aryl($C_{1-8}$)alkylene or heteroaryl($C_{1-8}$) alkylene;

each $R^7$ is independently halo, cyano, nitro, trifluoromethyl, azido, $C_{1-8}$alkyl, hydroxy, $NR_aR_b$, $C_{1-8}$alkoxy, aryloxy, —C(=O)$NR_aR_b$, —C(=S)$NR_aR_b$, —C(=$NR_c$)$NR_aR_b$, —$NR_c$C (=$NR_c$)$NR_aR_b$, —$NR_c$C (=S)$NR_aR_b$, —$NR_c$C(O)$NR_aR_b$, —$NR_c$C(NCN)$NR_aR_b$, aryl or heteroaryl;

X is $CR_dR_e$, O, S, —S(=O)—, —SO$_2$—, —C(=O)—, —C(=S)—or $NR^1$;

n is 0, 1, 2, or 3;

m is 0, 1, 2, 3 or 4;

$R_a$ and $R_b$ are each independently hydrogen, $C_{1-8}$alkyl, aryl, aryl($C_{1-8}$)alkylene, heteroaryl, or heteroaryl($C_{1-8}$) alkylene; or $R_a$ and $R_b$, together with the nitrogen to which they are attached, form a pyrrolidino, piperidino, morpholino, or thiomorpholino ring;

each $R_c$ is independently hydrogen, $C_{1-8}$alkyl, aryl($C_{1-8}$) alkylene or heteroaryl($C_{1-8}$)alkylene;

$R_d$ and $R_e$ are each independently hydrogen, $C_{1-8}$alkyl, aryl, aryl($C_{1-8}$)alkylene, heteroaryl, or heteroaryl($C_{1-8}$) alkylene;

the bond represented by ——— is a single bond or a double bond;

$R^8$ is absent when the bond represented by ——— is a double bond; or when the bond represented by ——— is a single bond, $R^8$ is hydrogen, halo, hydroxy, $C_{1-8}$alkyl, $C_{1-8}$alkoxy, aryl($C_{1-8}$)alkylene, heteroaryl($C_{1-8}$)alkylene, aryloxy($C_{1-8}$)alkylene or heteroaryloxy($C_{1-8}$)alkylene;

wherein any aryl or heteroaryl of $R^1$—$R^8$ and $R_a$—$R_e$ is optionally substituted with one or more (e.g. 1, 2, 3, or 4) halo, cyano, nitro, trifluoromethyl, azido, $C_{1-8}$alkyl, hydroxyl, $NR_fR_g$, $C_{1-8}$alkoxy, aryloxy, —C(=O)$NR_fR_g$, —C(=S)$NR_fR_g$, —C(=$NR_h$)$NR_fR_g$, —$NR_h$C(=$NR_h$)$NR_fR_g$, —$NR_h$C(=S)$NR_fR_g$, —$NR_h$C(O)$NR_fR_g$, —$NR_h$C(NCN)$NR_fR_g$, aryl or heteroaryl;

wherein $R_f$ and $R_g$ are each independently hydrogen, $C_{1-8}$alkyl, aryl, aryl($C_{1-8}$)alkylene, heteroaryl, or heteroaryl ($C_{1-8}$)alkylene; or $R_f$ and $R_g$, together with the nitrogen to which they are attached, form a pyrrolidino, piperidino, morpholino, or thiomorpholino ring;

each $R_h$ is independently hydrogen, $C_{1-8}$alkyl, aryl($C_{1-8}$) alkylene or heteroaryl($C_{1-8}$)alkylene;

wherein any alkylene is optionally partially unsaturated; or a pharmaceutically acceptable salt thereof.

In another aspect, the present invention also provides:

a pharmaceutical composition comprising a compound of Formula (I), or a pharmaceutically acceptable salt thereof, and a pharmaceutically acceptable excipient (the composition preferably comprises a therapeutically effective amount of the compound or salt);

a method for treating a disease or condition in a mammal (e.g. a human) in need thereof, wherein a 5-HT receptor is implicated and modulation of a 5-HT function is desired comprising administering a therapeutically effective amount of a compound of Formula (I), or a pharmaceutically acceptable salt thereof to the mammal;

a method for treating or preventing a disease or disorder of the central nervous system in a mammal in need thereof, comprising administering a therapeutically effective amount of a compound of Formula (I), or a pharmaceutically acceptable salt thereof to the mammal;

a compound of Formula (I) or a pharmaceutically acceptable salt thereof for use in medical diagnosis or therapy (e.g. the treatment of 5-HT related disease such as anxiety, obesity, depression, or a stress related disease);

the use of a compound of Formula (I), or a pharmaceutically acceptable salt thereof to prepare a medicament useful for treating or preventing a disease or disorder of the central nervous system in a mammal in need thereof; and a method for modulating 5-HT receptor function, comprising administering an effective modulatory amount of a compound of Formula (I), or a pharmaceutically acceptable salt thereof.

The invention also provides synthetic intermediates and processes disclosed herein that are useful for preparing compounds of Formula (I).

Compounds of Formula (I) are 5-HT ligands. Thus, radiolabeled compounds of Formula (I) are useful as imaging agents and biomarker for medical therapy and diagnosis. Such radiolabeled compounds are also useful as pharmacological tools for studying 5-HT function and activity. Accordingly, the invention also provides a radiolabeled compound of Formula (I), or a salt thereof.

Compounds of Formula (I) can be labeled using techniques which are well known in the art. For example, a radioisotope can be incorporated into the compound or appended to the compound of Formula (I) using techniques well known in the art. For example, see Arthur Murry III, D. Lloyd Williams; *Organic Synthesis with Isotopes,* vol. I and II, Interscience Publishers Inc., N.Y. (1958) and Melvin Calvin et al. *Isotopic Carbon* John Wiley and Sons Inc., N.Y. (1949). Any radioisotope capable of being detected can be employed as a label. For example, suitable radioisotopes include: carbon-11, fluorine-18, fluorine-19, iodine-123 and iodine-125. Preferably, a compound of Formula (I) may be labeled by appending one or more radioisotopes of a halogen (e.g. iodine-123) to an aromatic ring, or by alkylating a nitrogen of a compound of Formula (I) with a group comprising a phenyl group bearing a radioisotope.

The invention also provides a radiolabeled compound of Formula (I) for use in medical diagnosis or therapy, as well as the use of a radiolabeled compound of Formula (I) to prepare a medicament useful for medical diagnosis or therapy.

The invention also provides a method for imaging tissue comprising 5-HT receptors comprising contacting the tissue with a radiolabeled compound of the invention, and detecting the compound bound to said tissue.

DETAILED DESCRIPTION OF THE INVENTION

The compounds of the invention are useful for treating or preventing diseases or disorders of the central nervous system. Specific diseases or disorders of the central nervous system for which a compound of Formula (I) may have activity include, but are not limited to: obesity, depression, epilepsy, anxiety, Alzheimers disease, withdrawal from drug abuse, schizophrenia, schizophreniform disorder, schizoaffective disorder, delusional disorder, a stress related disease (e.g. general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine, headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific development disorder, agitation disorder, selective serotonin reuptake inhibition (SSRI) "poop out" syndrome or a Tic disorder (e.g., Tourette's syndrome).

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkylene can be partially unsaturated, the alkyl chain may comprise one or more (e.g. 1, 2, 3, or 4) double or triple bonds in the chain. Substituted $C_{1-8}$alkyl includes $C_{1-8}$alkyl substituted by fluoro, $C_{1-8}$alkoxy and aryl.

Aryl denotes a phenyl radical or an ortho-fused bicyclic carbocyclic radical having about eight to fourteen ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and $N(R_n)$ wherein $R_n$ is absent or is H, $C_{1-8}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "cycloalkyl" denotes a cyclic alkyl group having 3 to 8 carbon atoms. For example cyclopropyl, cyclobutyl, cyclopentyl, cyclohexyl. The term "substituted cycloalky" denotes a cycloalkyl substituted by $C_{1-8}$alkyl or aryl.

The term "Het" generally represents a non aromatic heterocyclic group, which can be saturated or partially unsaturated, containing at least one heteroatom (e.g., 1, 2, or 3) selected from the group consisting of oxygen, nitrogen, and sulfur. Specific, "Het" groups include monocyclic, bicyclic, or tricyclic groups containing one or more heteroatoms selected from the group consisting of oxygen, nitrogen, and sulfur. A "Het" group also can include one or more oxo groups (=O) attached to a ring atom. Nonlimiting examples of Het groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, thiomorpholine, and the like.

The term "alkylene" refers to a divalent straight or branched hydrocarbon chain (e.g., ethylene —$CH_2CH_2$—).

The term "aryl$C_{1-3}$alkylene" for example includes benzyl, phenethyl, naphthylmethyl and the like.

The term "rac" denotes racemic.

The term "treating" includes prophylaxis treatment.

The term "—S(O)—" denotes sulfoxide (S valence=4)

The term "—S(O)(O)—" denotes sulfone (S valence=6)

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine 5-HT activity using the standard tests which are well known in the art.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-8}$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, $C_{1-8}$alkyl can be methyl, ethyl, propyl, isopropyl, butyl, iso-butyl, sec-butyl, pentyl, 3-pentyl, hexyl, or heptyl; $C_{1-8}$alkoxy can be methoxy, ethoxy, propyloxy, isopropyloxy, butyloxy, iso-butyloxy, sec-butyloxy, pentyloxy, 3-pentyloxy, hexyloxy, 1-methylhexyloxy, or heptyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), pyridazinyl (or its N-oxide), indolyl, isoquinolyl (or its N-oxide) or quinolinyl (or its N-oxide).

Specific values for $R^1$ and $R^2$ independently are hydrogen, $C_{1-8}$ alkyl, substituted $C_{1-8}$ alkyl, aryl($C_{1-8}$)alkylene, cycloalkyl, substituted cycloalkyl or heteroaryl ($C_{1-8}$)alkylene.

Specific values for $R^3$ and $R^4$ independently are hydrogen, $C_{1-8}$alkyl or aryl($C_{1-8}$)alkylene.

Specific values for $R^1$, $R^2$, $R^3$ and $R^4$ independently are hydrogen or $C_{1-8}$alkyl.

A specific value for $R^1$, $R^2$, $R^3$ and $R^4$ independently is hydrogen.

A specific value for $R^1$, $R^2$, $R^3$ and $R^4$ independently is $C_{1-8}$alkyl.

A specific value for $R^5$ is hydrogen, $C_{1-8}$alkyl, aryl($C_{1-8}$) alkylene or aryl.

A specific value for $R^5$ is hydrogen or $C_{1-8}$alkyl.

A specific value for $R^5$ is hydrogen.

A specific value for $R^5$ is $C_{1-8}$alkyl.

Specific values for each $R^6$ independently are hydrogen, $C_{1-8}$alkyl, aryl($C_{1-8}$)alkylene or aryl.

Specific values for each $R^6$ independently are hydrogen or $C_{1-8}$alkyl.

A specific value for each $R^6$ independently is hydrogen.

A specific value for each $R^6$ independently is $C_{1-8}$alkyl.

A specific value for $R^7$ is aryl or heteroaryl.

A specific value for $R^7$ is halo, cyano, nitro, trifluoromethyl, azido, $C_{1-8}$alkyl, hydroxyl, $NR_aR_b$, $C_{1-8}$alkoxy, aryloxy, —C(=O)$NR_aR_b$, or —C(=S)$NR_aR_b$.

A specific value for $R^7$ is —C(=$NR_c$)$NR_aR_b$, —$NR_cC$(=$NR_c$)$NR_aR_b$, —$NR_cC$(=S)$NR_aR_b$, —$NR_cC$(O)$NR_aR_b$, or —$NR_cC$(NCN)$NR_aR_b$.

A specific value for $R^7$ is tetrazoyl or triazoyl.

A specific value for $R^8$ is absent when the bond represented by ——— is a double bond.

A specific value for $R^8$ when the bond represented by ——— is a single bond is hydrogen or $C_{1-8}$alkyl.
A specific value for X is $CH_2$, O or $NR^1$.
A specific value for X is O or $NR^1$.
A specific value for X is —O—.
A specific value for X is —S—, —S(=O)— or —$SO_2$—.
A specific value for X is —C(=O)— or —C(=S)—.
A specific value for n is 1 or 2.
A specific value for n is 1.
A specific value for n is 0.
A specific value for m is 0.
A specific value for m is 1 or 2.
A specific value for m is 1.
A specific value for m is 3 or 4.
A specific compound of Formula (I) is a compound of Formula (II):

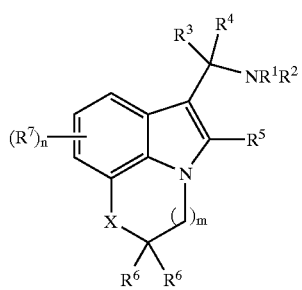

(II)

wherein $R^1$, $R^2$ $R^3$ $R^4$ $R^5$, $R^6$, $R^7$, n, m, and X have any of the values, specific values, more specific values, or preferred values described herein.

A specific compound of Formula (I) is a compound of Formula (III):

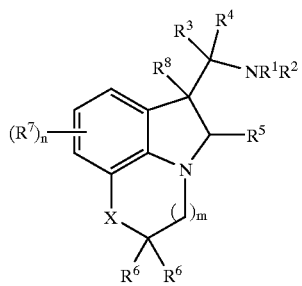

(III)

wherein $R^1$, $R^2$, $R^3$, $R^4$, $R^5$, $R^6$, $R^7$, n, m, and X have any of the values, specific values, more specific values, or preferred values described herein.

Specifically, the invention also provides a method for treating or preventing obesity, migraine, depression, epilepsy, anxiety, Alzheimers disease, withdrawal from drug abuse, schizophrenia, a stress related disease (e.g. general anxiety disorder), panic disorder, sleep disorders, a phobia, obsessive compulsive disorder, post-traumatic-stress syndrome, immune system depression, a stress induced problem with the gastrointestinal or cardiovascular system, or sexual dysfunction in a mammal (e.g. a human) comprising administering a therapeutically effective amount of a compound of Formula (I), or a pharmaceutically acceptable salt thereof to the mammal.

Specifically, the invention also provides a method of treating or preventing epilepsy, anxiety, Alzheimers disease, withdrawal from drug abuse, obesity, depression, or a stress related disease, comprising administering to a mammal (e.g. a human) in need of such treatment, a therapeutically effective amount of a compound of Formula (I) or a pharmaceutically acceptable salt thereof.

Specifically, the invention also provides the use of a compound of Formula (I) or a pharmaceutically acceptable salt thereof to prepare a medicament for treating or preventing obesity, depression, epilepsy, anxiety, Alzheimers disease, withdrawal from drug abuse, schizophrenia, a stress related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human).

Specifically, the invention also provides the use of a compound of Formula (I) or a pharmaceutically acceptable salt thereof to prepare a medicament for treating or preventing epilepsy, anxiety, Alzheimers disease, withdrawal from drug abuse, obesity, depression, or a stress related disease in a mammal (e.g. a human).

The invention also provides a method for preparing a compound of Formula (I) wherein $R^1$ or $R^2$ is hydrogen comprising deprotecting a corresponding compound of Formula (I) wherein $R^1$ and/or $R^2$ is a suitable nitrogen protecting group.

An intermediate particularly useful for preparing a compound of Formula (I) is a compound of Formula (IV):

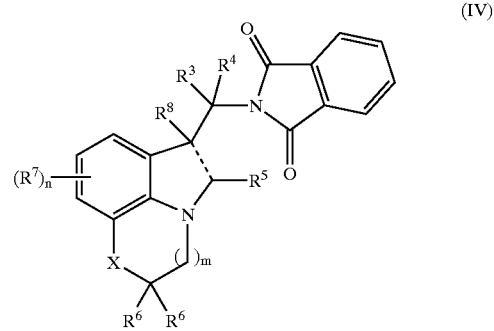

(IV)

wherein $R^3$, $R^4$, $R^5$, $R^6$, $R^7$, $R^8$, n, m, and X have any of the values, specific values, more specific values, or preferred values described herein.

Compounds of the invention can generally be prepared as illustrated in Scheme 1.

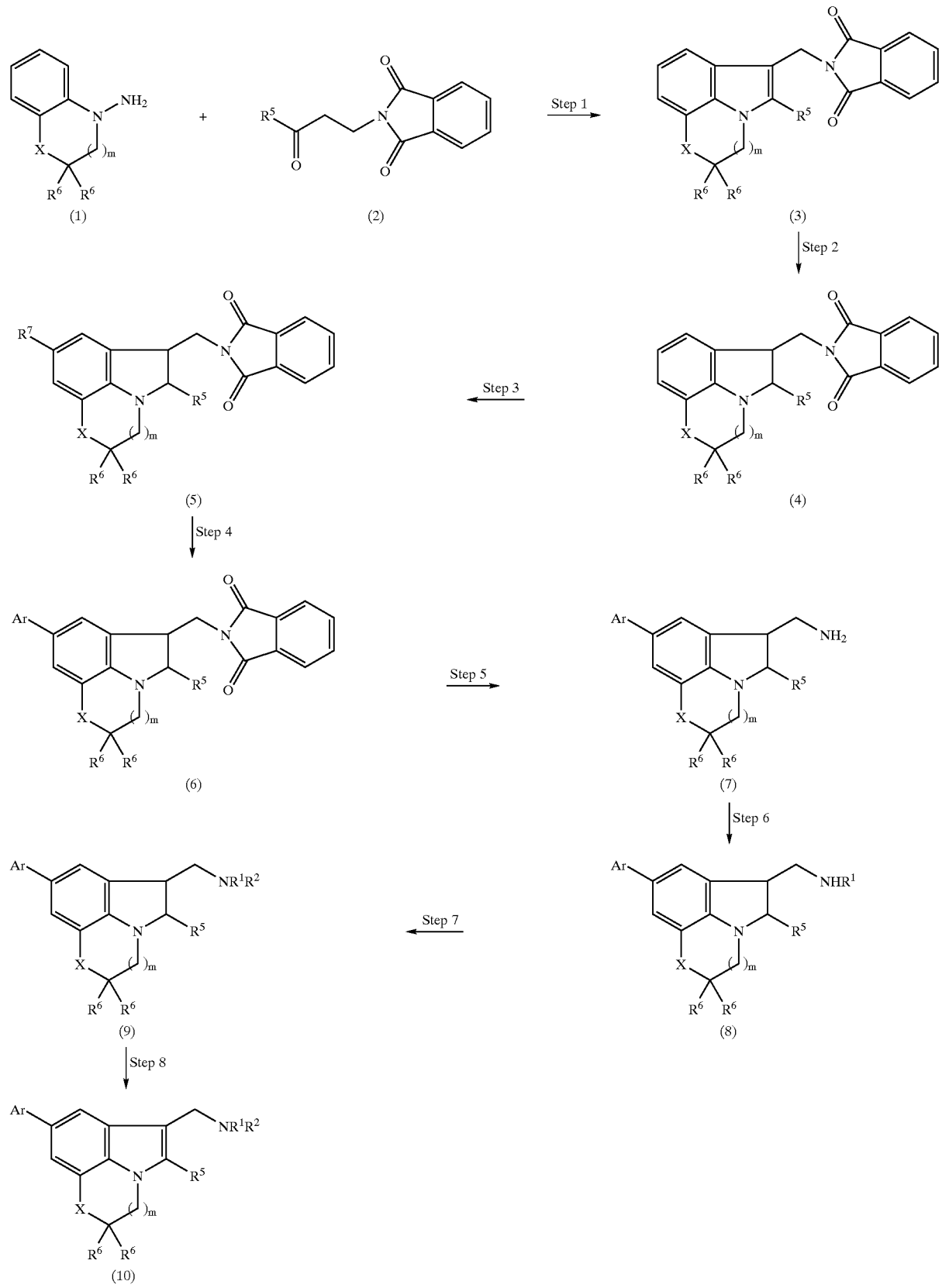

Starting materials 1 and 2 are commercially available or can be prepared by procedures that would be well known to one of ordinary skill in organic chemistry. The variables used in the Scheme 1 are as defined below or as in the claims. For the preparation of 1, see Scheme 4a, 4b and Scheme 5. The carbonyl compound 2 can be prepared by oxidizing the corresponding alcohol by methods well known in the art. The corresponding alcohols are commercially available or can be prepared by methods well known in the art. In step 1, the Fischer indole synthesis carried out in refluxing aqueous methanol provides indole 3 (see, "*Indoles, Best Synthetic Methods*" Academic Press, 1999, San Diego, Calif.). In step 2, Compound 3 can be reduced with sodium cyanoborohydride in an acidic media such as trifluoroacetic acid or acetic acid to give the indoline compound 4. In step 3, halogenation of 4 provides halogenated compound 5: using N-bromosuccinimide (NBS) in DMF provides $R_7$=Br, or using $I_2$/$CHCl_3$/$CF_3CO_2Ag$ provides $R_7$=I. In step 4, compound 5 can react with a variety of metallated (B, Sn, Al, Zn, Mg, etc.) aromatic reagents, in particular such as aryl boronic acids, under palladium (such as $Pd(PPh_3)_4$, $Pd_2(dba)_3$, $Pd(OAc)_2$, etc.) catalysis (see Miyaura, N. et al, *Chem Rev.* 1995, 95, 2457) to form the arylated indoles 6 (wherein Ar is aryl or heteroaryl). In step 5, the phthalimido group of the arylated indole 6 is cleaved by reaction with hydrazine to provide primary amine 7 (see "*Protective Groups in Organic Synthesis, 3rd Edition*" Greene and Wuts, 1999, John Wiley and Sons, Inc, New York).

In steps 6 and 7, the primary amine 7 can be derivatized, for example, with standard reductive alkylation conditions involving treatment with an aldehyde in the presence of sodium cyanoborohydride (see, for example, Lane, C. F., "Sodium Cyanoborohydride—A Highly Selective Reducing Agent for Organic Functional Groups", *Synthesis*, 1975, 135) to give indoline compounds of Formula (I) (i.e., the $R^1$ and $R^2$ substituted products 8 and/or 9). In step 8, the indoline compound 9 can be oxidized to generate indole compound 10 using an oxidation agent such as $MnO_2$, 2,3-dichloro-5,6-dicyano-1,4-benzoquinone (DDQ), or trichloroisocyanuric acid (see, for example, U. Tilstam, et al., *Tet. Lett.*, 2001, 42, 5385.

Compounds for where $R_8$ is other than H, Compound 11, can be prepared according to procedures shown in Scheme 2.

Scheme 2

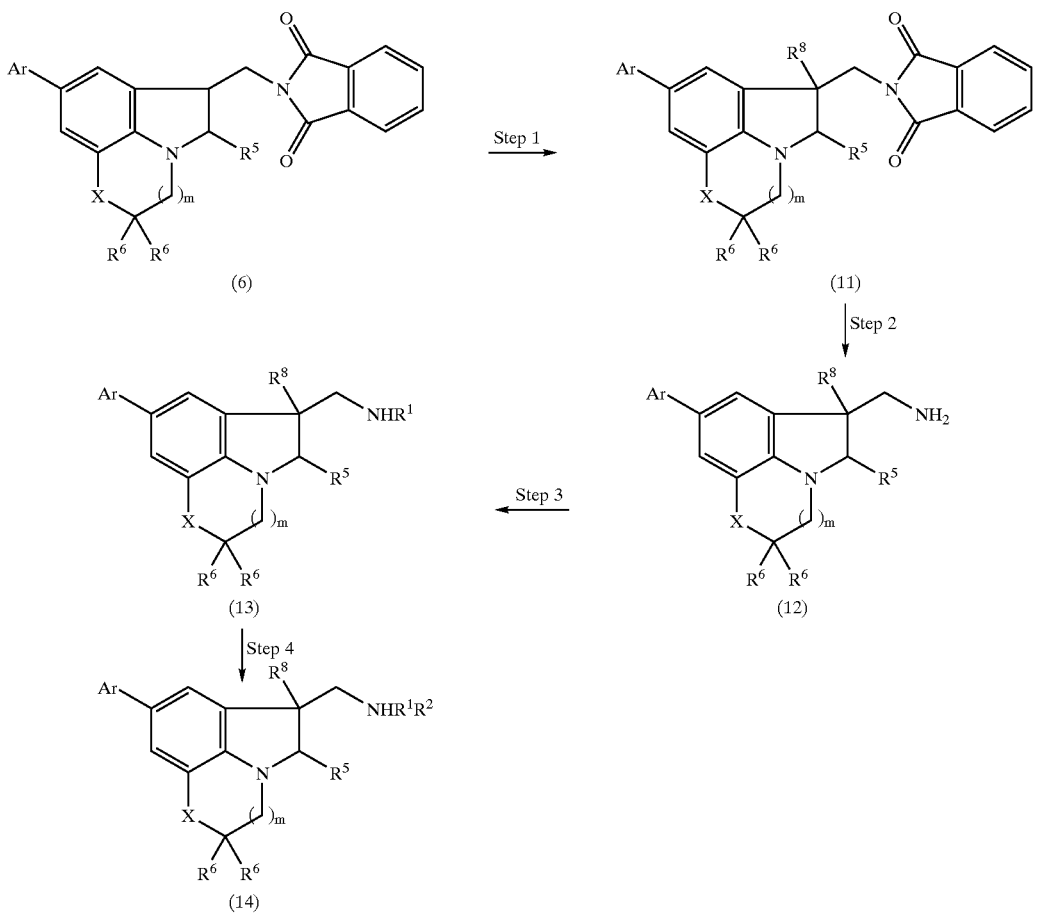

The variables used in Scheme 2 are as defined herein. In step 1, compound 6 can be alkylated with a strong base, such as lithium diisopropylamide (LDA) and an alkylating reagent, for example, MeI or EtI, to introduce alkyl moieties for $R^8$. In step 1, compound 6 can also be halogenated with a halogenating agent, (for example, NBS and a catalytic amount of benzoyl peroxide in $CCl_4$) to introduce a halogen atom for $R^8$. Utilizing steps 3 and 4, primary amine 11 can be converted to the indoline compounds secondary and tertiary amine compounds 13 and 14 using procedures well known in the art and discussed herein.

Compounds for where $R^8$ is other than H (for example, when $R^8$=alkyl), can also be prepared according to procedures discussed in Scheme 3.

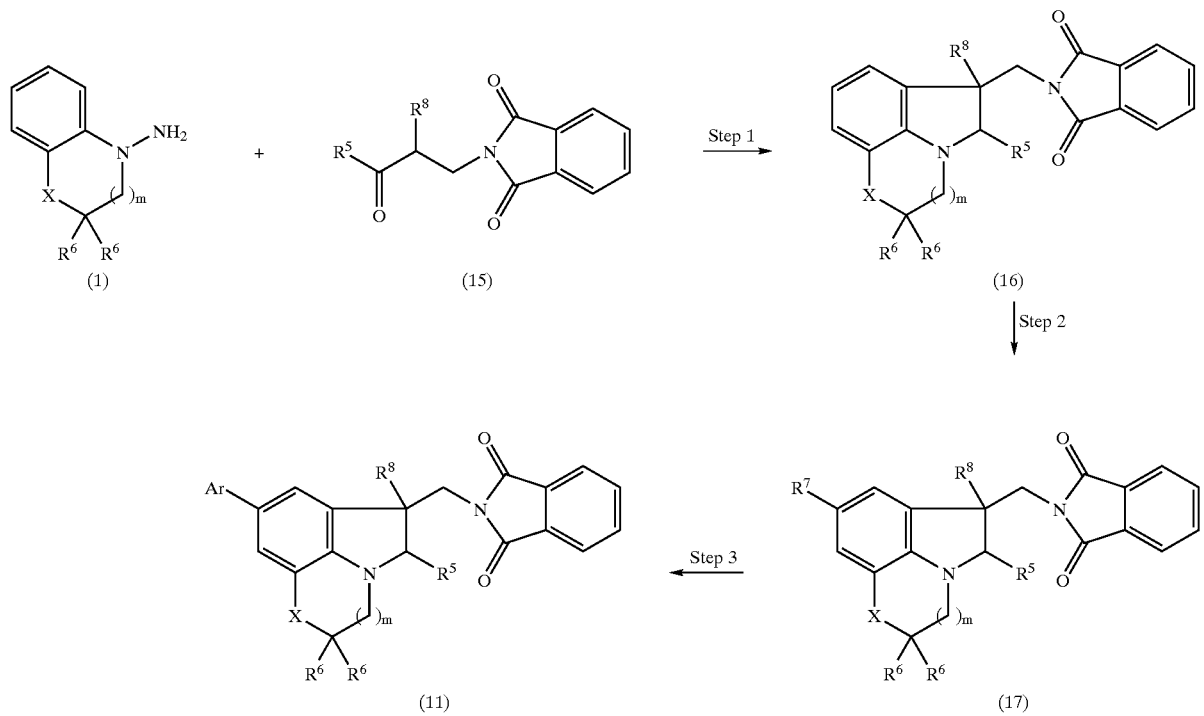

The variables used in the Scheme 3 are as defined herein. In step 1, reaction of the hydrazine compound 1 with the carbonyl compound 15 and then followed by reduction with a reducing agent such as sodium borohydride provides the indoline compound 16. In steps 2 and 3, compound 16 can be converted to the intermediates 17 and 11 using procedures well known in the art and discussed herein. Carbonyl compound 15 can be prepared by methods well known in the art. For example, utilizing methods for preparing the carbonyl compound described in Scheme 1.

The Fischer indole synthesis precursor 1 can be prepared, for example, as outlined in Scheme 4a and 4b.

-continued

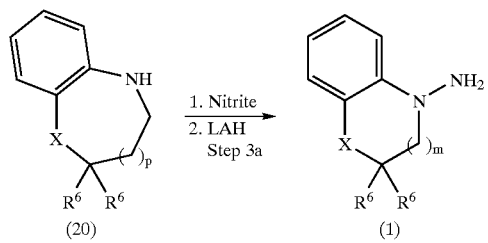

$m = p + 1$

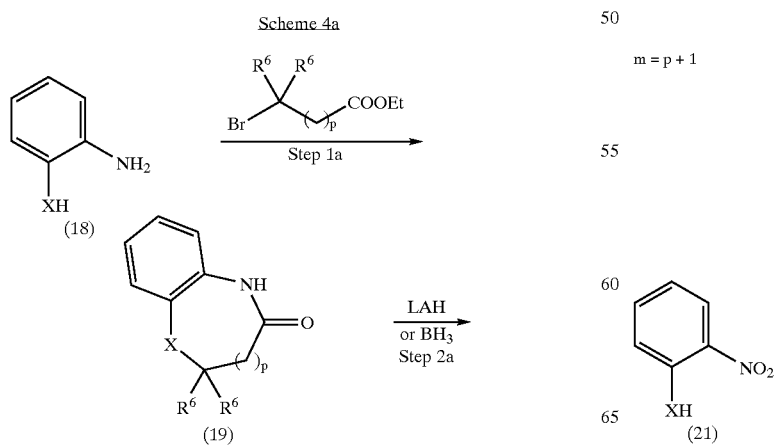

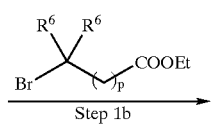

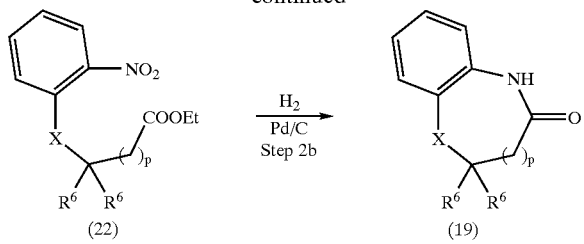

In step 1a, treatment of aminophenol 18 (X=O) or aminothiophenol (X=S) with a halogen substituted ester in the presence of a base such as potassium carbonate provides the bicyclic compound 19. In step 2a, reduction of 19 with a reducing agent such as lithium aluminum hydride or borane converted the lactam into the cyclic amine 20. In step 3a, treatment of 20 with, for example, isoamylnitrite and followed by reduction of the generated nitroso intermediate affords the hydrazine intermediate 1 that is used herein for Fischer indole synthesis.

In Scheme 4b, intermediate 19 can be prepared from the nitrophenol 21 (X=O or nitrothiophenol (X=S). In step 1b, reaction of 21 with a halogen substituted ester in the presence of base such as sodium hydride provides the alkylated intermediate 22. In step 2b, upon hydrogenolysis, the nitro group is reduced to the amino group and cyclized to form intermediate 19.

Still another method for preparation of the hydrazine intermediate 1 is shown in Scheme 5. In step 1, compound 21 is reacted with the halogen substituted aldehyde to form compound 23, which, in step 2, can be converted into intermediate 20 under hydrogenolysis.

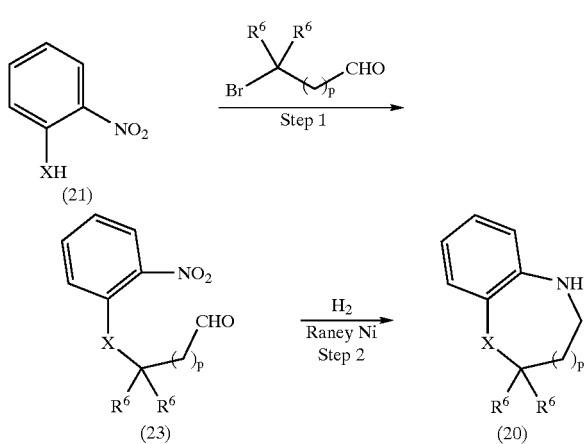

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, maleonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of Formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 50 mg/kg, preferably about 0.1 to about 50 mg/kg, and more preferably about 0.1 to about 10 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of Formula (I) that act as either agonists or as antagonists of one or more 5-HT receptor subtypes. The compounds of the invention are 5-HT ligands, which displace a radiolabeled test ligand from one or more 5-HT receptor subtype at a concentration of 1 $\mu$M. The procedures used for testing such displacement are well known and would be readily available to one skilled in the art. For example, see L. W. Fitzgerald et al., *Mol. Pharmacol*, 2000, 57, 1, 75–81; and D. B. Wainscott, et al., *J. Pharmacol Exp Ther*, 1996, 276, 2, 720–727.

DESCRIPTION OF PREFERRED EMBODIMENTS

The following Example and preparations are provided to illustrate the invention but are not intended to limit the scope of the invention.

Preparation of 2-(2,3-dihydro[1,4]oxazino[2,3,4-hi] indol-6-ylmethyl)-1H-isoindole-1,3(2H)-dione

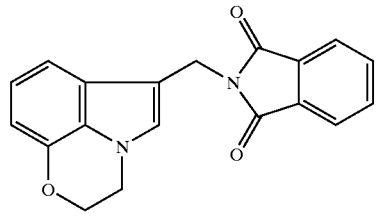

A mixture of 2,3-dihydro-4H-1,4-benzoxazin-4-amine hydrochloride (0.187 g, 1.0 mmol) and 3-(1,3-dioxo-1,3-dihydro-2H-isoindol-2-yl) (0.224 g, 1.1 mmol) in MeOH/H$_2$O (9/1) was heated at reflux for 14 h. After cooling down to rt, the mixture was concentrated in vacuo and the residue was subjected to preparative TLC (EtOAc/Hex., ½) to give 0.097 g (30%) of light yellow solid as the title compound: $^1$H NMR (400 MHz, CDCl$_3$) δ 7.84–7.81 (m, 2 H), 7.71–7.69 (m, 2 H), 7.48 (d, J=8.0 Hz, 1 H), 7.30 (s, 1 H), 7.04 (dd, J=8.0, 7.8 Hz, 1 H), 6.67 (d, J=7.8 Hz, 1 H), 5.04 (s, 2 H), 4.51–4.49 (m, 2 H), 4.26–4.24 (m, 2 H); MS (EI) m/z 319 (M$^+$+H).

Preparation of (rac)-2-(2,3,5,6-tetrahydro[1,4]oxazino[2,3,4-hi]indol-6-ylmethyl)-1H-isoindole-1,3(2H)-dione

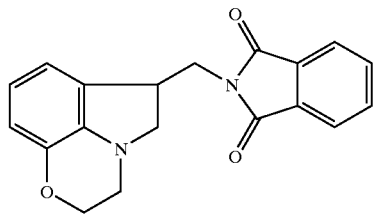

A freshly prepared solution of sodium cyanoborohydride (0.093 g, 1.48 mmol) in CH$_3$OH (0.3 mL) was added dropwise to a 0° C. solution of 2-(2,3-dihydro[1,4]oxazino[2,3,4-hi]indol-6-ylmethyl)-1H-isoindole-1,3(2H)-dione (0.094 g, 0.29 mmol) in TFA (3.0 mL). The mixture was stirred at rt for 1 hour and diluted with H$_2$O (10.0 mL) and made basic by the addition of 15% NaOH. The mixture was then extracted with EtOAc (3×). The combined EtOAc solution was dried over MgSO$_4$ and concentrated in vacuo to dryness. The residue was redissolved in CH$_2$Cl$_2$ and filtered. The filtrate was concentrated in vacuo to dryness and the residue was subjected to preparative TLC (EtOAc/Hex., ½) to give 0.031 g (33%) of light yellow oil as the title compound: $^1$H NMR (400 MHz, CDCl$_3$) δ 7.93–7.88 (m, 2 H), 7.80–7.75 (m, 2 H), 6.79–6.77 (m, 1 H), 6.75–6.65 (m, 2 H), 4.46–4.43 (m, 2 H), 4.10–4.05 (m, 1 H), 4.00–3.94 (m, 1 H), 3.77–3.73 (m, 1 H), 3.34–3.33 (m, 1 H), 3.30–3.26 (m, 1 H), 3.17–3.15 (m, 1 H), 3.10–3.08 (m, 1 H); MS (EI) m/z 321 (M$^+$+H).

Preparation of (rac)-2-[(8-bromo-2,3,5,6-tetrahydro[1,4]oxazino-[2,3,4-hi]indol-6-yl)methyl]-1H-isoindole-1,3(2H)-dione

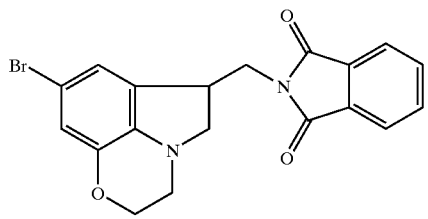

To a solution of (rac)-2-(2,3,5,6-tetrahydro[1,4]oxazino[2,3,4-hi]indol-6-ylmethyl)-1H-isoindole-1,3(2H)-dione (0.030 g, 0.094 mmol) in DMF (1.0 mL) was added the solution of N-bromosuccinimide (0.018 g, 0.098 mmol). The reaction mixture was stirred at room temperature for 1 hour and water (10.0 mL) was added. The aqueous solution was extracted with EtOAc (3×) and the combined EtOAc solution was dried over MgSO$_4$ and filtered. The filtrate was concentrated in vacuo to dryness to give 0.035 g (94%) of light yellow oil as the desired product: $^1$H NMR (400 MHz, CDCl$_3$) δ 7.82–7.79 (m, 2 H), 7.70–7.63 (m, 2 H), 6.81 (s, 1 H), 6.70 (s, 1 H), 4.34–4.29 (m, 2 H), 3.93–3.81 (m, 2 H), 3.63–3.59 (m, 1 H), 3.27–3.23 (m, 1 H), 3.19–3.15 (m, 1 H), 3.05–3.00 (m, 1 H), 2.98–2.89 (m, 1 H); MS (EI) m/z 399 (M$^+$+H), 401 (M$^+$+H).

Preparation of (rac)-2-[(8-iodo-2,3,5,6-tetrahydro[1,4]oxazino[2,3,4-hi]indol-6-yl)methyl]-1H-isoindole-1,3(2H)-dione

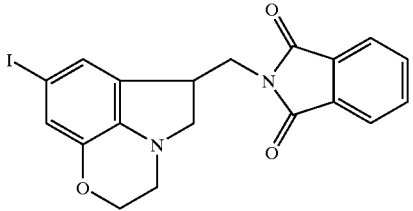

To a suspension of (rac)-2-(2,3,5,6-tetrahydro[1,4]oxazino[2,3,4-hi]indol-6-ylmethyl)-1H-isoindole-1,3(2H)-dione (0.081 g, 0.253 mmol) and silver trifluoroacetate (0.059 g, 0.266 mmol) in CHCl$_3$ (2.0 mL) was added a solution of iodine (0.067 g, 0.266 mmol) in CHCl$_3$ (8.0 mL) dropwise at rt. The mixture was stirred for 68 h. Silver trifluoroacetate (0.03 g, 0.136 mmol) and solution of iodine (0.035 g, 0.136 mmol) in CHCl$_3$ (6.0 mL) were added. The mixture was stirred at rt for 4 h and added again silver trifluoroacetate (0.02 g, 0.09 mmol) and solution of iodine (0.025 g, 0.10 mmol) in CHCl$_3$ (5.0 mL). After stirring for another 2 h, the mixture was filtered through a pad of celite and washed with CHCl$_3$. The filtrate was washed with Na$_2$SO$_3$ solution and dried (MgSO$_4$). After filtration, the filtrate was concentrated in vacuo to dryness and the residue was subjected to prep TLC (EtOAc/hexane, 1:2) to give 0.046 g (41%) of light yellow oil as the title compound: $^1$H NMR (400 MHz, CDCl$_3$) δ 7.81–7.78 (m, 2 H), 7.69–7.65 (m, 2 H), 6.98 (s, 1 H), 6.86 (s, 1 H), 4.34–4.29 (m, 2 H), 3.91-3.80 (m, 2 H), 3.62–3.58 (m, 1 H), 3.24–3.14 (m, 2 H), 3.04–3.00 (m, 1 H), 2.97–2.92 (m, 1 H); MS (EI) m/z 447 (M$^+$+H).

Preparation of (rac)-2-{[8-(2,4-dichlorophenyl)-2,3,5,6-tetrahydro[1,4]oxazino[2,3,4-hi]indol-6-yl]methyl}-1H-isoindole-1,3(2H)-dione

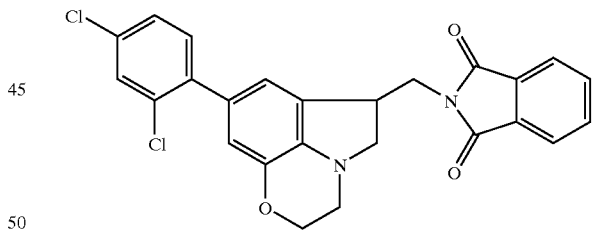

A mixture of (rac)-2-[(8-iodo-2,3,5,6-tetrahydro[1,4]oxazino[2,3,4-hi]indol-6-yl)methyl]-1H-isoindole-1,3(2H)-dione (0.044 g, 0.098 mmol), 2,4-dichlorophenylboronic acid (0.028 g, 0.147 mmol), tetrakis(triphenylphosphine)palladium (0.011 g, 0.01 mmol) and K$_2$CO$_3$ (0.054 g, 0.39 mmol) in THF-DMA (1:1, 2.0 mL) was heated at 66° C. for 2 h. 2,4-Dichlorophenylboronic acid (0.02 g, 0.105 mmol), tetrakis(triphenyl-phosphine)palladium (0.007 g, 0.006 mmol) and K$_2$CO$_3$ (0.02 g, 0.145 mmol) were added and heat was continued for 24 h. 2,4-Dichlorophenylboronic acid (0.02 g, 0.105 mmol) and tetrakis(triphenyl-phosphine)palladium (0.007 g, 0.006 mmol) were again added and heat was continued for another 3 h. After cooling down to rt, water (10.0 mL) and EtOAc (10.0 mL) were added and separated. The aqueous layer was extracted with EtOAc (2×). The combined EtOAc solution was dried over MgSO$_4$ and filtered. The filtrate was concentrated in vacuo to dryness. The residue was subjected to prep TLC (EtOAc/hexane, 1:2) to give 0.015 g (32%) of colorless solid as the title compound: $^1$H NMR (400 MHz, CDCl$_3$) δ 7.92–7.90 (m, 2 H), 7.81–7.78 (m, 2 H), 7.45 (d, J=2.0 Hz, 1 H), 7.27–7.18 (m, 2 H), 6.80 (s, 1 H), 6.74 (s, 1 H), 4.51–4.47 (m, 2 H), 4.13–4.09 (m, 1 H), 4.03–3.97 (m, 1 H), 3.83–3.79 (m, 1 H), 3.46–3.42 (m, 1 H), 3.38–3.35 (m, 1 H), 3.23–3.19 (m, 1 H), 3.16–3.14 (m, 1 H).

EXAMPLE 1

(rac) [8-(2,4-Dichlorophenyl)-2,3,5,tetrahydro[1,4]oxazino-[2,3,4-hi]indol-6-yl]methanamine

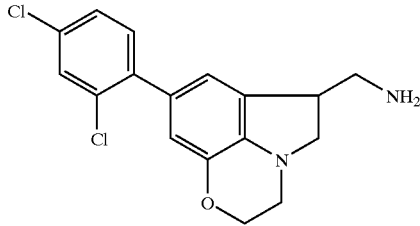

A mixture of 2-{[8-(2,4-dichlorophenyl)-2,3,5,6-tetrahydro[1,4]oxazino-[2,3,4-hi]indol-6-yl]methyl}-1H-isoindole-1,3(2H)-dione (0.036 g, 0.078 mmol) and hydrazine monohydrate (0.05 mL, 0.051 g, 1.03 mmol) in CH$_3$OH (2.0 mL) and CH$_2$Cl$_2$ (2.0 mL) was stirred at rt for 14 hours and filtered. After concentrating in vacuo to dryness, the residue was subjected to column chromatography (silica gel, 2% CH$_3$OH/CHCl$_3$ and 1% NH$_4$OH) to afford the title compound: $^1$H NMR (400 MHz, CDCl$_3$) δ 7.49–7.48 (m, 1 H), 7.31–7.26 (m, 2 H), 6.84 (s, 1 H), 6.73 (s, 1 H), 4.50–4.48 (m, 2 H), 3.57–3.53 (m, 1 H), 3.42–3.37 (m, 1 H), 3.30–3.27 (m, 1 H), 3.19–3.10 (m, 3 H), 3.04–3.01 (m, 1 H); MS (EI) m/z 335 (M$^+$+H), 337 (M$^+$+H).

The invention has been described with reference to various specific and preferred embodiments and techniques. However, it should be understood that many variations and modifications may be made while remaining within the spirit and scope of the invention.

What is claimed:

1. A compound of Formula I:

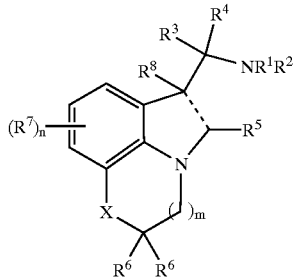

wherein:

$R^1$ and $R^2$ are independently hydrogen, C$_{1-8}$alkyl, substituted C$_{1-8}$alkyl, aryl(C$_{1-8}$)alkylene, cycloalkyl, substituted cycloalkyl or heteroaryl (C$_{1-8}$)alkylene;

$R^3$ and $R^4$ are independently hydrogen, C$_{1-8}$alkyl, aryl(C$_{1-8}$)alkylene, or heteroaryl (C$_{1-8}$)alkylene;

$R^5$ and each $R^6$ are independently hydrogen, C$_{1-8}$alkyl, aryl, heteroaryl, aryl(C$_{1-8}$)alkylene or heteroaryl(C$_{1-8}$)alkylene;

each $R^7$ is independently halo, cyano, nitro, trifluoromethyl, azido, C$_{1-8}$alkyl, hydroxy, NR$_a$R$_b$, C$_{1-8}$alkoxy, aryloxy, —C(=O)NR$_a$R$_b$, —C(=S)NR$_a$R$_b$, —C(=NR$_c$)NR$_a$R$_b$, —NR$_c$C(=NR$_c$)NR$_a$R$_b$, —NR$_c$C(=S)NR$_a$R$_b$, —NR$_c$C(O)NR$_a$R$_b$, —NR$_c$C(NCN)NR$_a$R$_b$, aryl or heteroaryl;

X is O;

n is 0, 1, 2, or 3;

m is 1;

$R_a$ and $R_b$ are each independently hydrogen, C$_{1-8}$alkyl, aryl, aryl(C$_{1-8}$)alkylene, heteroaryl, or heteroaryl(C$_{1-8}$)alkylene; or $R_a$ and $R_b$, together with the nitrogen to which they are attached, form a pyrrolidino, piperidino, morpholino, or thiomorpholino ring;

each $R_c$ is independently hydrogen, C$_{1-8}$alkyl, aryl(C$_{1-8}$)alkylene or heteroaryl(C$_{1-8}$)alkylene;

$R_d$ and $R_e$ are each independently hydrogen, C$_{1-8}$alkyl, aryl, aryl(C$_{1-8}$)alkylene, heteroaryl, or heteroaryl(C$_{1-8}$)alkylene;

the bond represented by ——— is a single bond or a double bond;

$R^8$ is absent when the bond represented by ——— is a double bond; or when the bond represented by ——— is a single bond, $R^8$ is hydrogen, halo, hydroxy, C$_{1-8}$alkyl, C$_{1-8}$alkoxy, aryl(C$_{1-8}$)alkylene, heteroaryl (C$_{1-8}$)alkylene, aryloxy(C$_{1-8}$)alkylene or heteroaryloxy (C$_{1-8}$)alkylene;

wherein any aryl or heteroaryl of $R^1$–$R^8$ and $R_a$–$R_e$ is optionally substituted with one to four halo, cyano, nitro, trifluoromethyl, azido, C$_{1-8}$alkyl, hydroxyl, NR$_f$R$_g$, C$_{1-8}$alkoxy, aryloxy, —C(=O)NR$_f$R$_g$, —C(=S)NR$_f$ R$_g$, —C(=NR$_h$)NR$_f$R$_g$, —NR$_h$C(=NR$_h$) NR$_f$R$_g$, —NR$_h$C(=S) NR$_f$R$_g$, —NR$_h$C(O) NR$_f$R$_g$, —NR$_h$C(NCN)NR$_f$R$_g$, aryl or heteroaryl;

wherein $R_f$ and $R_g$ are each independently hydrogen, C$_{1-8}$alkyl, aryl, aryl(C$_{1-8}$)alkylene, heteroaryl, or heteroaryl(C$_{1-8}$)alkylene; or $R_f$ and $R_g$, together with the nitrogen to which, they are attached, form a pyrrolidino, piperidino, morpholino, or thiomorpholino ring;

each $R_h$ is independently hydrogen, C$_{1-8}$alkyl, aryl(C$_{1-8}$)alkylene or heteroaryl(C$_{1-8}$)alkylene;

wherein any alkylene is optionally partially unsaturated;

or a pharmaceutically acceptable salt thereof.

2. The compound of claim 1, wherein $R^1$ is hydrogen, C$_{1-8}$alkyl, aryl(C$_{1-8}$)alkylene.

3. The compound of claim 1, wherein $R^1$ is hydrogen.

4. The compound of claim 1, wherein $R^1$ is C$_{1-8}$alkyl.

5. The compound of claim 1, wherein $R^2$ is hydrogen, C$_{1-8}$alkyl, aryl(C$_{1-8}$)alkylene.

6. The compound of claim 1, wherein $R^2$ is hydrogen.

7. The compound of claim 1, wherein R 2 is C$_{1-8}$alkyl.

8. The compound of claim 1, wherein R3 is hydrogen, C$_{1-8}$alkyl, or aryl(C$_{1-8}$)alkylene.

9. The compound of claim 1, wherein $R^3$ is hydrogen.

10. The compound of claim 1, wherein $R^3$ is C$_{1-8}$alkyl.

11. The compound of claim 1, wherein $R^4$ is hydrogen, C$_{1-8}$alkyl, or aryl(C$_{1-8}$)alkylene.

12. The compound of claim 1, wherein $R^4$ is hydrogen.

13. The compound of claim 1, wherein $R^4$ is C$_{1-8}$alkyl.

14. The compound of claim 1, wherein $R^5$ is hydrogen, fluoro, C$_{1-8}$alkyl, aryl, or aryl(C$_{1-8}$)alkylene.

15. The compound of claim 1, wherein $R^5$ is hydrogen or C$_{1-8}$alkyl.

16. The compound of claim 1, wherein $R^5$ is hydrogen.

17. The compound of claim 1, wherein each $R^6$ is independently hydrogen, fluoro, $C_{1-8}$alkyl, aryl, or aryl($C_{1-8}$)alkylene.

18. The compound of claim 1, wherein each $R^6$ is independently hydrogen or $C_{1-8}$alkyl.

19. The compound of claim 1, wherein each $R^6$ is independently hydrogen.

20. The compound of claim 1, wherein each $R^6$ is independently fluoro.

21. The compound of claim 1, wherein $R^7$ is aryl or heteroaryl.

22. The compound of claim 1, wherein $R^7$ is halo, cyano, nitro, trifluoromethyl, azido, $C_{1-8}$alkyl, hydroxy, $NR_aR_b$, $C_{1-8}$alkoxy, aryloxy, —C(=O)$NR_aR_b$, or —C(=S)$NR_aR_b$.

23. The compound of claim 1, wherein $R^7$ is —C(=$NR_c$)$NR_aR_b$, —$NR_cC$(=$NR_c$)$NR_aR_b$, —$NR_cC$(=S)$NR_aR_b$, —$NR_cC$(O)$NR_aR_b$, or —$NR_cC$(NCN)$NR_aR_b$.

24. The compound of claim 1, wherein $R^7$ is tetrazoyl or triazoyl.

25. The compound of claim 1, wherein $R^8$ is absent, and the bond represented by ——— is a double bond.

26. The compound of claim 1, wherein $R^8$ is hydrogen or $C_{1-8}$alkyl, and the bond represented by ——— is a single bond.

27. The compound of claim 1, wherein n is 1 or 2.

28. The compound of claim 1, wherein n is 1.

29. The compound of claim 1, wherein n is 0.

30. The compound of claim 1, wherein $R^1$ or $R^2$ independently substituted $C_{1-8}$alkyl, cycloalkyl or substitituted cycloalkyl.

31. The compound of claim 1, which is [8-(2,4-dichlorophenyl)-2,3,5-tetrahydro[1,4]oxazino-[2,3,4-hi]indol-6-yl]methanamine; or a pharmaceutically acceptable salt thereof.

32. A compound according to Formula IV:

(IV)

wherein $R^3$ and $R^4$ are independently hydrogen, $C_{1-8}$alkyl, aryl($C_{1-8}$)alkylene, or heteroaryl($C_{1-8}$)alkylene;

$R^5$ and each $R^6$ are independently hydrogen, $C_{1-8}$alkyl, aryl, heteroaryl, aryl($C_{1-8}$)alkylene or heteroaryl($C_{1-8}$)alkylene;

each $R^7$ is independently halo, cyano, nitro, trifluoromethyl, azido, $C_{1-8}$alkyl, hydroxy, $NR_aR_b$, $C_{1-8}$alkoxy, aryloxy, —C(=O)$NR_aR_b$, —C(=S)$NR_aR_b$, —C(=$NR_c$)$NR_aR_b$, —$NR_cC$(=$NR_c$)$NR_aR_b$, —$NR_cC$(=S)$NR_aR_b$, —$NR_cC$(O)$NR_aR_b$, —$NR_cC$(NCN)$NR_aR_b$, aryl or heteroaryl;

X is O;

n is 0, 1, 2, or 3;

m is 1;

$R_a$ and $R_b$ are each independently hydrogen, $C_{1-8}$alkyl, aryl, aryl($C_{1-8}$)alkylene, heteroaryl, or heteroaryl($C_{1-8}$)alkylene; or $R_a$ and $R_b$, together with the nitrogen to which they are attached, form a pyrrolidino, piperidino, morpholino, or thiomorpholino ring;

each $R_c$ is independently hydrogen, $C_{1-8}$alkyl, aryl($C_{1-8}$)alkylene or heteroaryl($C_{1-8}$)alkylene;

$R_d$ and $R_e$ are each independently hydrogen, $C_{1-8}$alkyl, aryl, aryl($C_{1-8}$)alkylene, heteroaryl, or heteroaryl($C_{1-8}$)alkylene;

the bond represented by ——— is a single bond or a double bond;

$R^8$ is absent when the bond represented by ——— is a double bond; or when the bond represented by ——— is a single bond, $R^8$ is hydrogen, halo, hydroxy, $C_{1-8}$alkyl, $C_{1-8}$alkoxy, aryl($C_{1-8}$)alkylene, heteroaryl($C_{1-8}$)alkylene, aryloxy($C_{1-8}$)alkylene or heteroaryloxy($C_{1-8}$)alkylene;

wherein any aryl or heteroaryl of $R^1$—$R^8$ and $R_a$—$R_e$ is optionally substituted with one to four halo, cyano, nitro, trifluoromethyl, azido, $C_{1-8}$alkyl, hydroxyl, $NR_fR_g$, $C_{1-8}$alkoxy, aryloxy, —C(=O)$NR_fR_g$, —C(=S)$NR_f R_g$, —C(=$NR_h$)$NR_fR_g$, —$NR_hC$(=$NR_h$)$NR_fR_g$, —$NR_hC$(=S)$NR_fR_g$, —$NR_hC$(O)$NR_fR_g$, —$NR_hC$(NCN)$NR_fR_g$, aryl or heteroaryl;

wherein $R_f$ and $R_g$ are each independently hydrogen, $C_{1-8}$alkyl, aryl, aryl($C_{1-8}$)alkylene, heteroaryl, or heteroaryl($C_{1-8}$)alkylene; or $R_f$ and $R_g$, together with the nitrogen to which they are attached, form a pyrrolidino, piperidino, morpholino, or thiomorpholino ring; and each $R_h$ is independently hydrogen, $C_{1-8}$alkyl, aryl($C_{1-8}$)alkylene or heteroaryl($C_{1-8}$)alkylene;

wherein any alkylene is optionally partially unsaturated.

33. A pharmaceutical composition comprising a compound of claim 1 and a pharmaceutically acceptable excipient.

34. A method for treating a disease or disorder of the central nervous system in a mammal in need thereof selected from the group consisting of anxiety, depressing, panic disorder, obessive compulsive disorder, schizophrenia, epilepsy, migraine, obesity or withdrawal from drug abuse, comprising administering a therapeutically effective amount of a compound of claim 1 to the mammal.

* * * * *